United States Patent [19]

Kawabe et al.

[11] Patent Number: 4,776,384
[45] Date of Patent: Oct. 11, 1988

[54] METHOD FOR MONITORING COPPER-ALLOY TUBES FOR MAINTAINING CORROSION RESISTANCE AND CLEANLINESS FACTOR OF THEIR INNER SURFACES

[75] Inventors: Atsushi Kawabe, Sakai; Katsumi Yasui, Nishinomiya; Masaki Yamamoto, Akashi; Koji Nagata, Aichi; Tetsuro Atsumi, Nagoya; Mamoru Nishikawa, Mie, all of Japan

[73] Assignees: Sumitomo Light Metal Industries, Ltd., Tokyo; The Kansai Electric Power Co., Inc., Osaka, both of Japan

[21] Appl. No.: 933,910

[22] Filed: Nov. 24, 1986

[30] Foreign Application Priority Data

Nov. 28, 1985 [JP] Japan ............................... 60-267699

[51] Int. Cl.⁴ ........................... F28G 1/12; F28G 9/00
[52] U.S. Cl. ........................................ 165/1; 165/95; 165/133; 15/3.51; 134/8; 134/22.1
[58] Field of Search ............................. 165/95, 1, 133; 15/3.51; 134/8, 22.1

[56] References Cited

U.S. PATENT DOCUMENTS

| | | |
|---|---|---|
| 3,788,962 | 1/1974 | Frenck . |
| 4,033,407 | 7/1977 | Quintilliano ............................. 165/1 |
| 4,390,058 | 6/1983 | Otake et al. .............................. 165/1 |
| 4,476,917 | 10/1984 | Otake et al. ............................. 165/95 |

FOREIGN PATENT DOCUMENTS

| | | |
|---|---|---|
| 0030459 | 6/1981 | European Pat. Off. . |
| 0155826 | 9/1985 | European Pat. Off. . |
| 1087475 | 2/1955 | France . |
| 3125546 | 3/1982 | Fed. Rep. of Germany . |
| 1016361 | 1/1966 | United Kingdom . |
| 2125171 | 2/1984 | United Kingdom . |

OTHER PUBLICATIONS

Japanese Patent Abstract 58-208587; vol. 8 No. 57 (M-283) [1494] Mar. 15, 1984.
Japanese Patent Abstract 58-171578; vol. 8 No. 3 (C-203) [1440] Jan. 7, 1984.
"A Method for Determining Corrosion Rates from Linear Polarization Data" Milton Stern, pp. 60-64.

Primary Examiner—Albert W. Davis, Jr.
Assistant Examiner—John K. Ford
Attorney, Agent, or Firm—Parkhurst, Oliff & Berridge

[57] ABSTRACT

A method of monitoring the inner surfaces of copper-alloy condenser tubes of a condenser through which seawater flows as a coolant by controlling a ferrous-ion injecting operation to inject ferrous ions into the coolant for forming a protective film on the inner surfaces of the condenser tubes, and a sponge-ball cleaning operation to clean the inner tube surfaces by passing sponge balls through the condenser tubes. During an initial period of exposure of the condenser tubes to the coolant after installation of the condenser tubes in the condenser, the ferrous ions are injected into the coolant to form the protective film on the inner surfaces of the condenser tubes until the polarization resistance of the condenser tubes has reached $10^4 \Omega cm^2$. Subsequently, the ferrous-ion injecting operation and the sponge-ball cleaning operation are executed while the polarization resistance and heat transfer rate of the condenser tubes are monitored. The injecting and cleaning operations are performed to maintain within suitable ranges the polarization resistance and the heat transfer rate of the condenser tubes. These ranges may vary, depending upon whether the coolant is non-chlorinated seawater, chlorinated seawater, or sulfide-ion polluted seawater.

8 Claims, 3 Drawing Sheets

A: INITIAL PERIOD OF EXPOSURE TO SEAWATER
B: NON-CHLORINATED SEAWATER
C: CHLORINATED SEAWATER
D: SULFIDE-ION POLLUTED SEAWATER

A: INITIAL PERIOD OF EXPOSURE TO SEAWATER
B: NON-CHLORINATED SEAWATER
C: CHLORINATED SEAWATER
D: SULFIDE-ION POLLUTED SEAWATER

METHOD FOR MONITORING COPPER-ALLOY TUBES FOR MAINTAINING CORROSION RESISTANCE AND CLEANLINESS FACTOR OF THEIR INNER SURFACES

BACKGROUND OF THE INVENTION

1. Field of the Invention

The present invention relates in general to a method suitable for monitoring the corrosion resistance and fouling condition of copper-alloy condenser tubes, through which seawater or estuary water typically flows, and more particularly to a method of maintaining the condition of the inner surfaces of the condenser tubes such that their corrosion resistance and heat transfer rate are optimized.

2. Discussion of the Prior Art and its Problems

Copper-alloy condenser tubes of a condenser which uses seawater (this term being interpreted to include water of estuary or bay) as a coolant have been conventionally maintained by (a) protecting the inner surfaces against corrosion, and (b) preventing deposition or accumulation of various suspended matters and corrosion products on the inner surfaces of the tubes, and thus avoiding the deterioration of heat transfer characteristics of the tubes. Described more specifically, it has been found extremely effective to inject ferrous ions in the form of ferrous sulfate into the coolant for increasing the corrosion resistance of the condenser tubes, and to pass sponge balls through the condenser tubes for cleaning the inner surface of the tubes to remove the deposited matters.

While the corrosion resistance of the condenser tubes is remarkably improved by a protective film of ferric hydroxide formed of ferrous ions injected in the form of ferrous sulfate, for example, it is also known that such a protective film will reduce the heat transfer characteristics of the condenser tubes. On the other hand, although cleaning the condenser tubes with sponge balls enhances the heat transfer of the tubes, it may also cause a decline in the corrosion resistance of the tubes if the protective film on the inner tube surface is excessively removed by the sponge-ball cleaning. Thus, there is a general recognition that the ferrous-ion injection and the sponge-ball cleaning are not satisfactorily stable and reliable for maintaining required corrosion resistance and heat transfer characteristics of the condenser tubes. In light of the above drawbacks, it has been proposed to inject ferrous ions and introduce sponge balls into the condenser tubes according to a program which is predetermined based on laboratory tests or field tests, so as to satisfy the two requirements, i.e., corrosion resistance and heat transfer rate of the condenser tubes. The program to carry out the ferrous-ion injection and sponge-ball cleaning is modified or revised as needed, based on the results of periodic inspection of the condenser tubes.

However, the nature of the cooling seawater is not kept constant during the service of the condenser. More particularly, the conditions of the seawater such as degree of pollution, condition of marine life, and concentration of slimes or sludges may change from time to time. Accordingly, the depth of a protective film resulting from the injection of a given amount of ferrous sulfate and the amount of foreign matter deposited after each sponge-ball cleaning may differ depending upon the changing conditions of the seawater introduced into the condenser tubes. Therefore, a continuous operation of a condenser with predetermined constant rate of ferrous-ion injection and sponge-ball cleaning is not considered a proper way to maintain the condenser tubes in the optimum conditions from the standpoint of corrosion resistance and heat transfer characteristics. Excessive corrosion or deterioration of heat transfer rate of the condenser tubes may cause economical losses due to non-productive time necessary for replacement of the tubes, increased fuel cost due to reduced thermal efficiency, and other undesirable factors that lead to lowering the operating efficiency of a plant in which the condenser is installed.

Such economical losses due to corrosion or deteriorated heat transfer characteristics of the condenser tubes have been increasingly experienced in the industry because of a recent growing tendency toward expansion of capacity of power plants, or continuous operation of nuclear power plants. In order to overcome these drawbacks a method is provided for monitoring the corrosion resistance and heat transfer characteristics of condenser tubes, in order to control the injection of ferrous ions and the introduction of sponge-balls in response to information obtained by the monitoring, to optimize the anti-corrosion and heat transfer characteristics of the condenser tubes.

SUMMARY OF THE INVENTION

It is therefore an object of the present invention to provide a method of monitoring the inner surface of condenser tubes, and controlling ferrous-ion injecting and sponge-ball cleaning operations so as to maintain optimum corrosion resistance and heat transfer rate of the condenser tubes, despite varying the nature of the coolant which flows through the condenser tubes.

The above object may be attained by the present invention, which provides a method of monitoring the inner surface of copper-alloy condenser tubes of a condenser wherein seawater or estuary water, which may at various times be non-chlorinated, chlorinated, or polluted with sulfide ions, is caused to flow as a coolant, and controlling a ferrous-ion injecting operation to inject ferrous ions into the coolant for forming a corrosion-resistant film on the inner surface of the condenser tubes, and a sponge-ball cleaning operation to clean the inner surface of the condenser tubes by passing sponge balls through the condenser tubes, comprising the steps of: during an initial period of exposure of the condenser tubes to the coolant after installation of the condenser tubes in the condenser, injecting the ferrous ions into the coolant to form a protective film on the inner surface of the condenser tubes until the polarization resistance of the condenser tubes has reached $10^4$ $\Omega cm^2$; and subsequently executing the ferrous-ion injecting operation and the sponge-ball cleaning operation, depending on the nature of the coolant, while detecting the polarization resistance and heat transfer rate of the condenser tubes such that (a) while the coolant is non-chlorinated, the polarization resistance is not less than $5 \times 10^3$ $\Omega cm^2$ and the heat transfer rate of the condenser tubes is not less than the reference value of the condenser tubes, (b) while the coolant is chlorinated, the polarization resistance is not less than $2 \times 10^4$ $\Omega cm^2$ and the heat transfer rate is not less than the reference value of the condenser tubes, and (c) while the coolant is polluted with sulfide ions, the polarization resistance is not less than $5 \times 10^3$ $\Omega cm^2$ and the heat transfer rate is not less than a value which is about 10% lower than the reference value of the condenser tubes.

As described above, the method of the present invention is adapted to control the operation of a ferrous-ion injecting device for forming a protective film on the inner surfaces of the condenser tubes, and the operation of a sponge-ball supply device for cleaning the inner tube surfaces with sponge balls, depending upon the operation period of the condenser and the nature of the seawater introduced as a coolant flowing through the condenser tubes, so that the corrosion resistance and the heat transfer rate of the condenser tubes may be optimized. Thus, the present method is effective to eliminate the conventionally experienced economical losses due to corrosion of the condenser tubes, and/or increased fuel cost of the condenser due to deteriorated heat transfer rate of the condenser tubes. The contributions of the present invention are of important industrial significance.

BRIEF DESCRIPTION OF THE DRAWINGS

The above and optional objects, features and advantages of the present invention will be better understood by reading the following detailed description of the invention, when considered in connection with the accompanying drawings, in which.

DETAILED DESCRIPTION OF THE INVENTION

The present invention will be described in detail, by reference to the accompanying drawings.

Figure 1:
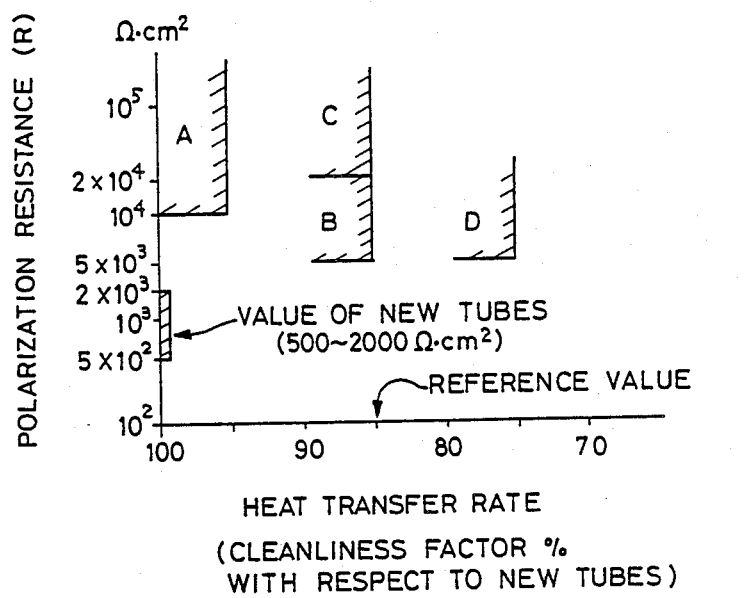
FIG. 1 is a graph showing ranges of polarization resistance and cleanliness factor of the inner surfaces of condenser tubes, according to a method of the invention for maintaining optimum corrosion resistance and heat transfer rate of the condenser tubes.

Referring first to the schematic view of FIG. 1, there are shown optimum ranges of the polarization resistance and cleanliness factor of the condenser tubes of a condenser, which are established according to the principle of the present invention, depending upon the operation period of the condenser, and the nature of the seawater which is introduced as a coolant flowing through the condenser tubes. That is, the present method is effective to control the corrosion protection and surface cleaning equipment provided for the condenser, i.e., the ferrous-ion (i.e. as ferrous sulfate) injecting device and the sponge-ball supply device, so that the corrosion resistance, as represented by the polarization resistance, and the heat transfer rate which corresponds to the cleanliness factor are optimized.

The polarization resistance R ($\Omega cm^2$) of the condenser tubes is defined as expressed by the following Equation (1):

$$R = (E_0/I_0)^2 (2\pi^2 a^3/\rho) \qquad (1)$$

where, $E_0$ = cathodically polarized value from natural potential: usually, 200 mV approx.

$I_0$ = current (mA) per condenser tube, with the above value $a$ = inside diameter (cm) of condenser tubes $\rho$ = resistivity ($\Omega cm$) of coolant The cleanliness factor (C), which is one of values representative of the heat transfer rate of the condenser tubes, is a ratio of a reference overall heat transfer coefficient ($K_0$) and an actual overall heat transfer coefficient ($K_1$). This ratio is calculated from the following Equation (2):

$$C = (K_1/K_0) \times 100 (\%) \qquad (2)$$

Figure 2A:
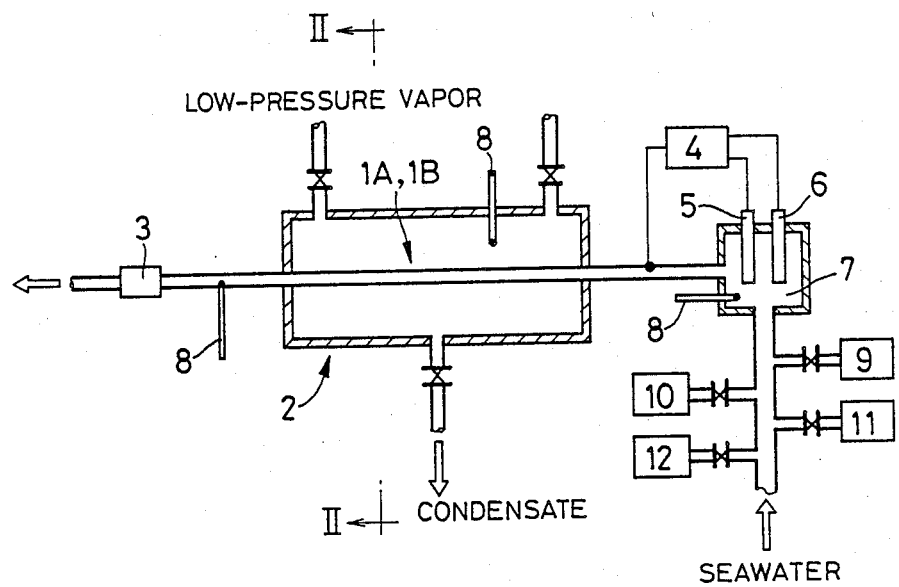
FIG. 2(a) is a view schematically showing a simulated arrangement of a condenser used in Examples according to the invention.

The reference overall heat transfer coefficient ($K_0$) is obtained from the following Equation (3):

$$K_0 = C_1 \times \sqrt{V} \qquad (3)$$

where, $C_1$ = constant determined by material and wall thickness of condenser tubes $V$ = average flow rate of coolant through condenser tubes The actual overall heat transfer coefficient ($K_1$) is calculated from the following Equation (4):

$$K = [W \times r \times C_p \times (t_2 - t_1)]/(A_s \times \theta_m) \qquad (4)$$

where, $W$ = flow rate of coolant through condenser tubes $r$ = specific gravity of coolant $C_p$ = specific heat of coolant $t_2$ = temperature of coolant at outlet end of condenser tubes $t_1$ = temperature of coolant at inlet end of condenser tubes $A_s$ = cooling surface area, i.e., total area of the portions of all condenser tubes which are cooled $\theta_m$ = logarithmic mean temperature difference The value $\theta_m$ is calculated from the following Equation (5):

$$\theta_m = (t_2 - t_1)/ln[(t_s - t_1)/(t_s - t_2)] \qquad (5)$$

where, $t_s$ = hot well temperature, i.e., the temperature of condensate held in the hot well (condenser shell), e.g., as measured in the interior of the condenseer shell 2 (see FIG. 2(a))

As an alternative to using the cleanliness factor to represent the heat transfer rate of the condenser tubes, it is possible to use a degree of vacuum at a suitable location outside the condenser tubes, within the condensing zone of the condenser. A decrease in the measured vacuum represents a change in the heat transfer rate. In either case, the change in the heat transfer rate may be detected by instruments such as a thermometer, a vacuum gauge and a flow meter, which are usually provided for the condenser system. The term "reference value" of the heat transfer rate used herein is interpreted to mean a value at which the condenser is sufficiently operable to perform its intended functions, even though the condenser tubes are somewhat contaminated or fouled with foreign substances deposited on their inner surfaces. Generally, the reference value is held within a range of 75-95%, usually around 85%, of the nominal heat transfer rate, i.e., the heat transfer rate of new condenser tubes.

It is known that the resistance to corrosion of copper-alloy condenser tubes through which seawater is passed is considerably improved if anti-corrosion or protective films or layers are formed on the inner surfaces of the condenser tubes during an initial period of exposure of the tubes to the seawater. Such protective films may be advantageously formed by injection of ferrous ions into the seawater before of while it flows through the condenser tubes, practically, by addition and subsequent dissolution of ferrous sulfate or other suitable water-soluble iron compounds. The protective films formed by injection of the ferrous ions may serve to effectively protect the condenser tubes against corrosion by the seawater, if the films have a polarization resistance of $10^4$ $\Omega cm^2$ or higher. According to the method of the present invention, the protective films as described above are first formed on the inner surfaces of the condenser tubes, during the initial period of exposure to the seawater. In this initial period, the cleaning of the inner tube surfaces with sponge balls is effected as needed, so that the cleanliness factor (representative of the heat transfer rate) of the condenser tubes is at least 95% of the nominal value of the condenser tubes (cleanliness factor of new condenser tubes).

After the effective protective films are formed on the inner surfaces of the condenser tubes immediately after the new condenser tubes are exposed to the seawater for the first time, the corrosion resistance and the fouling or contamination of the inner surfaces of the tubes are controlled, depending upon the nature of the seawater introduced into the condenser on a regular basis, in response to the polarization resistance and the heat transfer rate (cleanliness factor) of the condenser tubes, which are continuously monitored or detected.

Described in greater detail, in the case (a) where the seawater as the coolant is not chlorinated and is relatively less corrosive to the condenser tubes, the need to positively form the protective films by injection of ferrous ions is not so high. In this case (a), therefore, the injection of the ferrous ions is accomplished so that the polarization resistance does not fall below a comparatively low lower limit of $5 \times 10^3$ $\Omega cm^2$. On the other hand, the accumulation of marine life or slimes on the inner surfaces of the tubes proceeds at a relatively high rate where the non-chlorinated seawater flows through the tubes. In other words, the cleanliness factor of the inner tube surfaces is lowered at a relatively high rate. Accordingly, it is necessary to prevent the cleanliness factor from falling below the predetermined reference value, while the polarization resistance is held above the the lower limit indicated above. The recovery of the cleanliness factor may be easily achieved by cleaning the inner tube surfaces with sponge balls.

In the case (b) where the coolant used for the condenser is chlorinated seawater and is comparatively corrosive to the condenser tubes, the need to form the corrosion resistance by the ferrous-ion injection is accordingly high. In this case, therefore, the ferrous-ion injection is carried out so as to maintain a polarization resistance of at least $2 \times 10^4$ $\Omega cm^2$. While the accumulation of marine life or slimes is almost negligible, the cleanliness factor is considerably lowered due to the formation of the corrosion-resistant ferric hydroxide films by means of the ferrous-ion injection. In this case, too, the cleanliness factor must be kept above the predetermined reference level, while the above-indicated lower limit of the polarization resistance is maintained.

In the case (c) where the cooling water is polluted seawater containing a large amount of sulfide ions, the ferrous-ion injection and the sponge-ball cleaning are performed as described below.

It is noted that the seawater near a plant in which the condenser is installed may be polluted only in a limited period of the summer season, depending upon the location of the plant. This polluted seawater is highly corrosive to the condenser tubes due to sulfide ions contained therein. If the condenser tubes made of a copper alloy are not provided with initially formed protective films, they are heavily corroded by the polluted seawater. However, the condenser tubes having the initially formed protective films according to the invention are suitably protected by the films against corrosion by such polluted seawater for a few or several months. In the present case (c), the ferrous-ion injection is accomplished so as to keep the polarization resistance above $5 \times 10^3$ $\Omega cm^2$. On the other hand, a considerably large amount of ferric hydroxide and ferrous sulfide is deposited on the inner tube surfaces. The latter deposit is as a result of corrosion of the ferrous ions contained in the seawater, or ferrous materials of the piping parts of the condenser, by the sulfide ions contained in the seawater. This ferrous sulfide film in addition to the ferric hydroxide film, lowers the cleanliness factor of the condenser tubes at a remarkably higher rate in case (c) than in case (b). While the cleanliness factor may be recovered by cleaning the inner tube surfaces by using sponge balls, an excessive degree of cleaning of the inner tube surface with the sponge balls may cause the copper-alloy material of the tubes to be exposed, leading to heavy corrosion of the tubes. In light of this possibility, it is necessary that the sponge-ball cleaning of the condenser tubes be effected so that the cleanliness factor is not lower than about 75% of the nominal value, i.e., not below a lower limit which is about 10% lower than the predetermined reference value.

In case (c), after the pollution period of the seawater has passed, the sponge-ball cleaning of the inner surface of the condenser tubes must be carried out comparatively frequently, in order to remove as much as possible the substances deposited on the inner tube surface during the pollution period. Subsequently, protective films, as formed during the initial period of exposure of the new tubes to the seawater, must be formed on the inner surfaces of the condenser tubes, as previously described, so that the ferrous-ion injection and the sponge-ball cleaning may be subsequently effected according to the conditions of the case (a) or (b) discussed above.

Generally, the ferrous-ion injection by adding ferrous sulfate or other water-soluble iron compounds to the seawater (coolant) is accomplished so that the concentration of ferrous ions falls within a range of 0.03–0.5 ppm. The lower limit of 0.03 ppm is a required minimum for forming an effective protective film or layer on the inner surface of the condenser tubes, while the upper limit of 0.5 ppm is an allowable maximum beyond which the discharged seawater is colored to an extent which exceeds the allowable limit of environmental pollution.

The sponge-ball cleaning according to the invention is carried out with sponge balls which are commonly used for cleaning condenser tubes. Generally, the sponge balls used according to the invention have a diameter about 2 mm larger than the inside diameter of the condenser tubes. These sponge balls are introduced into the condenser in a suitable number for each cleaning cycle. The introduced sponge balls are fed with the coolant into the condenser tubes, and are passed through the tubes, whereby the inner surface of the tubes are cleaned by the sponge balls.

The advantages of the method of the present invention described above will be better understood from the following Examples, which are shown and described in comparison with the conventional method. However, it is to be understood that the present invention is by no means limited to the details of the illustrated Examples.

EXAMPLE 1

Figure 2B:
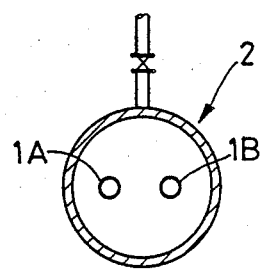
FIG. 2(b) is a schematic view in cross section taken along line II—II of FIG. 2(a)

Two aluminum brass tubes (JIS-H3300-C6871: seamless brass tubes for a condenser) 1A and 1B having an outside diameter of 25.4 mm, a wall thickness of 1.24 mm and a length of 3000 mm were set in a simulated condenser, as shown in FIGS. 2(a) and 2(b). The tubes 1A and 1B were maintained in terms of corrosion resistance and contamination of their inner surfaces, according to the method of the present invention, and the conventional method, respectively, as described below in detail.

The simulator shown in FIGS. 2(a) and 2(b) includes an intermediate heat exchange portion (condenser shell) 2 which is 1.5 m long, and has two water chambers 7 each of which accommodates devices or instruments necessary to measure the polarization resistance of the tubes 1A and 1B. These devices or instruments consist of a potentiostat 4, an anode 5 and a reference electrode 6. The simulator further includes a flow meter 3, a thermometer 8, a ferrous-ion injecting device 9, a sponge-ball supply device 10, a continuous seawater inspecting device 11, and a sulfide-ion injecting device 12, as shown in FIG. 2(a), for each of the two tubes 1A and 1B. As indicated in FIG. 2(b), the two tubes 1A and 1B were disposed in parallel, so as to extend through the heat exchange portion 2. Seawater was introduced into the two tubes 1A and 1B, through mutually independent supply lines. In FIG. 2(a), only the sea water supply line for the tube 1A is shown. The two tubes 1A and 1B were exposed at their outer surfaces to a low-pressure vapor introduced into the heat exchange portion 2.

With the two tubes 1A and 1B set in the simulated condenser, the condenser was operated for one month, with the tubes 1A and 1B maintained in the different conditions as described below, while the polarization resistance and the cleanliness factor of the tubes were monitored according to the Equations (1) and (2) previously indicated. The tube 1B was subjected to ordinary maintenance conditions as established in a condenser in a common power plant.

Maintenance Conditions for Tube 1A
Polarization Resistance:
The ferrous-ion injecting device 9 was operated to continuously inject 0.3 ppm of ferrous ions ($Fe^{++}$) into the seawater flowing through the tube 1A, so that the polarization resistance was $3 \times 10^4 \, \Omega cm^2$.

Heat Transfer Rate:
When the cleanliness factor of the tube 1A dropped below 95% of the nominal value, the sponge-ball supply device 10 was actuated to cause 12 sponge balls of appropriate size to pass through the tube 1A, for cleaning the inner surface of the tube.

Maintenance Conditions for Tube 1B
The ferrous-ion injecting device 9 and the sponge-ball supply device 10 were operated, irrespective of the detected polarization resistance and cleanliness factor of the tube 1B. Namely, the ferrous-ion injecting device 9 was operated to inject 0.3 ppm of ferrous ions into the seawater flowing the the tube 1B, five times per week, for 10 hours per day. The sponge-ball supply device 10 was not operated at all, and no sponge-ball cleaning was effected.

Figure 3A:
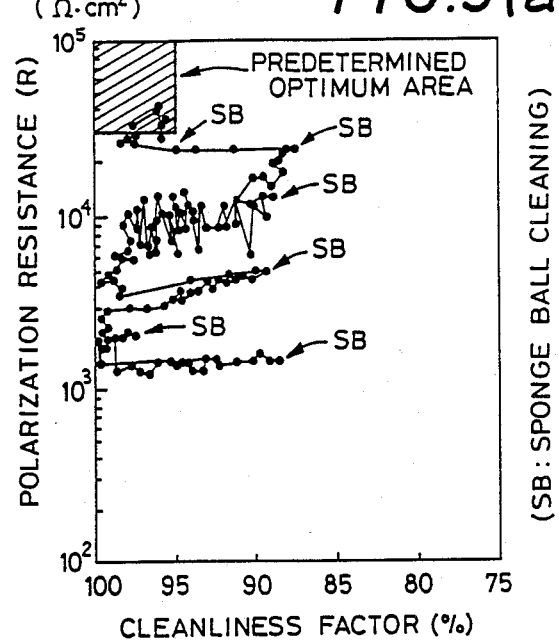
FIGS. 3(a) and 3(b) are graphs indicating changes in the polarization resistance and cleanliness factors of the condenser tubes of Example 1.
Figure 3B:
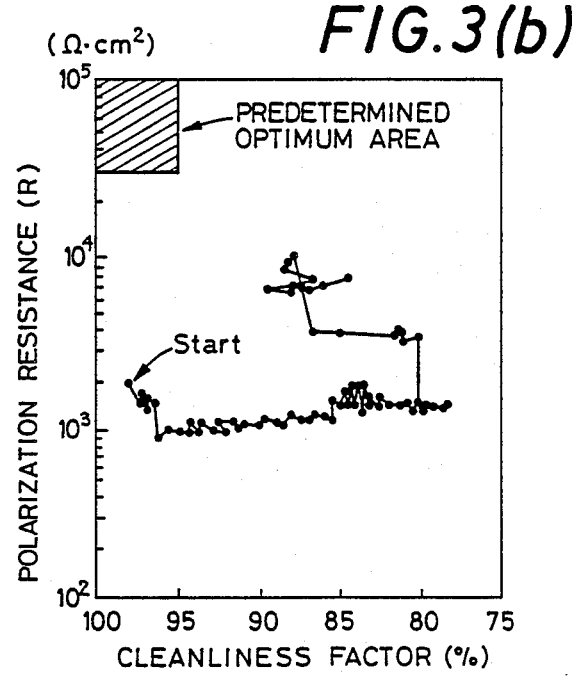

The one-month experimental operation of the condenser with the two tubes 1A and 1B produced the results as shown in the graphs of FIGS. 3(a) and 3(b), which indicate changes in the polarization resistance and cleanliness factor of the tubes 1A and 1B, respectively. It will be apparent from the graph of FIG. 3(a) that a protective film having a desired corrosion resistance was formed on the inner surface of the tube 1A, during the one-month exposure to the seawater according to the present invention. On the other hand, the graph of FIG. 3(b) shows that the polarization resistance of the tube 1B after the one-month exposure to the seawater according to the conventional method is considerably lower than that of the tube 1A according to the present invention, indicating that the protective film formed on the tube 1B is inferior to the film formed on the tube 1A. Further, the graph of FIG. 3(b) shows that the cleanliness factor of the tube 1B is lower than that of the tube 1A.

EXAMPLE 2

The two tubes 1A and 1B used in Example 1 were further exposed to the seawater and subjected to sponge balls for an additional period of six months, under the following conditions. After the experiment was over, the tubes 1A and 1B were removed from the simulated condenser equipment, and were cut in longitudinal cross-sectional plane, for inspecting the depth of corrosion of the inner surface. The measured corrosion depths are indicated in Table 1. As is apparent from the table, the cleanliness factor and the corrosion depth of the tube 1A maintained according to the present method are far better than those of the tube 1B maintained according to the conventional method.

Seawater Used:
For the first week, the tubes 1A and 1B were exposed to clean seawater. For the next week, the tubes 1A and 1B were exposed to seawater which contained 0.1 ppm of sulfide ions injected by the sulfide-ion injecting device 12. This two-week exposure cycle was repeated.

Maintenance Conditions for Tube 1A
While the tube 1A was exposed to the clean seawater, the ferrous-ion injection and the sponge-ball cleaning were effected so that the polarization resistance of the tube was not less than $10^4 \, \Omega cm^2$, while the cleanliness factor was not less than 85% of the nominal value. While the tube 1A was exposed to the sulfide-ion polluted seawater, the ferrous-ion injection and the sponge-ball cleaning were not effected. After the exposure to the polluted seawater was completed, 20 sponge balls were continuously introduced so as to pass through the tube 1A, for cleaning the inner surface of the tube 1A.

Maintenance Conditions for Tube 1B
Irrespective of the nature of the seawater, whether clean or polluted, the ferrous-ion injecting device 9 was operated for three hours each day, to inject 0.3 ppm of ferrous ions into the seawater, and the sponge-ball supply device 10 was operated two times a week, to introduce six sponge balls for each operation.

TABLE 1

| Tubes | Amount of Deposit on Inner Surface | Cleanliness Factor | Max. Corrosion Depth |
| --- | --- | --- | --- |
| 1A | 1.7 mg/cm$^2$ | 89% | less than 0.01 mm |

TABLE 1-continued

| Tubes | Amount of Deposit on Inner Surface | Cleanliness Factor | Max. Corrosion Depth |
|---|---|---|---|
| 1B | 4.5 mg/cm² | 78% | 0.2 mm |

What is claimed is:

1. A method of monitoring the inner surfaces of copper-alloy condenser tubes of a condenser wherein seawater or estuary water is caused to flow as a coolant through the condenser tubes by (1) controlling a ferrous-ion injecting operation to inject ferrous ions into said coolant for forming a protective film on the inner surfaces of said condenser tubes, and (2) controlling a sponge-ball cleaning operation to clean the inner surfaces of said condenser tubes by passing sponge balls through the condenser tubes, the method comprising the steps of:

during an initial period of exposure of said condenser tubes to said coolant after installation of the condenser tubes in the condenser, injecting the ferrous ions into said coolant to form a protective film on the inner surfaces of the condenser tubes until the polarization resistance of the condenser tubes has reached $10^4$ $\Omega cm^2$; and subsequently detecting the polarization resistance and heat transfer rate of said condenser tubes and executing said ferrous-ion injecting and sponge-ball cleaning operations, simultaneously or individually, depending upon the nature of said coolant, such that (a) while the coolant is non-chlorinated, when said polarization resistance falls below $5 \times 10^3$ $\Omega cm^2$, said sponge-ball cleaning operation is not conducted and said ferrous-ion injecting operation is conducted and when the heat transfer rate of said condenser tubes falls below a reference value for the condenser tubes, said sponge-ball cleaning operation is conducted and said ferrous-ion injecting operation is not conducted, (b) while the coolant is chlorinated, when the polarization resistance falls below $2 \times 10^4$ $\Omega cm^2$, said sponge-ball cleaning operation is not conducted and said ferrous-ion injecting operation is conducted and when said heat transfer rate falls below said reference value for the condenser tubes, said sponge-ball cleaning operation is conducted and said ferrous-ion injecting operation is not conducted and (c) while the coolant is polluted with sulfide ions, when said polarization resistance falls below $5 \times 10^3$ $\Omega cm^2$, said sponge-ball operation is not conducted and said ferrous-ion injecting operation is conducted and when said heat transfer rate falls below 90% of said reference value for the condenser tubes, said sponge-ball cleaning operation is conducted and said ferrous-ion injecting operation is not conducted.

2. A method according to claim 1, wherein said heat transfer rate is detected by measuring a reference overall heat transfer coefficient and an actual overall heat transfer coefficient of said condenser tubes.

3. A method according to claim 1, wherein said heat transfer rate is detected by measuring a degree of vacuum at a location outside said condenser tubes, in a condensing zone of said condenser.

4. A method according to claim 1, wherein said reference value is between 75% and 90% of the nominal heat transfer rate of the condenser tubes.

5. A method according to claim 1, wherein said sponge-ball cleaning operation is effected during said initial period, such that the heat transfer rate is not less than 95% of the nominal heat transfer rate of the condenser tubes.

6. A method for prolonging the useful life and enhancing the performance of a condenser, the method comprising passing coolant through condenser tubes contained in a condenser unit which includes means for detecting the polarization resistance of the condenser tubes, the polarization resistance being indicative of the corrosion resistance of the condenser tubes, and means for detecting the heat transfer rate of the condenser tubes, the coolant comprising cooling water which at different times may be non-chlorinated, chlorinated, or polluted with sulfide ions;

injecting ferrous ions into the coolant during an initial period of exposure of the condenser tubes to the coolant to form a protective film on the inner surfaces of the condenser tubes until the polarization resistance of the condenser tubes reaches about $10^4$ $\Omega cm^2$; and subsequently (1) monitoring the polarization resistance and the heat transfer rate of the condenser tubes and (2) injecting ferrous ions into the coolant and passing sponge balls through the condenser tubes in response to the measured polarization resistance and heat transfer rate such that (a) while the cooling water is non-chlorinated, when the polarization resistance falls below about $5 \times 10^3$ $\Omega cm^2$, said sponge-ball cleaning operation is not conducted and said ferrous-ion injecting operation is conducted and when the heat transfer rate falls below a reference value for the condenser tubes, said sponge-ball cleaning operation is conducted and said ferrous-ion injecting operation is not conducted; (b) while the cooling water is chlorinated, when the polarization resistance falls below about $2 \times 10^4$ $\Omega cm^2$, said sponge-ball cleaning operation is not conducted and said ferrous-ion injecting operation is conducted and when the heat transfer rate falls below said reference value for the condenser tubes, said sponge-ball cleaning operation is conducted and said ferrous-ion injecting operation is not conducted; and (c) while the cooling water is polluted with sulfide ions, when the polarization resistance falls below $5 \times 10^3$ $\Omega cm^2$, said sponge-ball cleaning operation is not conducted and said ferrous-ion injecting operation is conducted and when the heat transfer rate falls below 90% of said reference value for the condenser tubes, said sponge-ball cleaning operation is conducted and said ferous-ion injecting operation is not conducted.

7. A method for producing a corrosion resistant condenser tube having high resistance to corrosion and high heat transfer characteristics during an initial period of installation of the tube in a condenser unit in which coolant is caused to flow through the tube, the condenser unit including means for detecting the polarization resistance of the condenser tube, the polarization resistance being indicative of the corrosion resistance of the condenser tube, and means for detecting the heat transfer rate of the condenser tube, the method comprising:

passing coolant through the condenser tube, the coolant comprising cooling water which may be non-chlorinated, chlorinated, or polluted with sulfide ions;

injecting ferrous ions into the coolant to form a protective film on the inner surface of the condenser tube and passing sponge balls through the condenser tube to clean the inner surface of the condenser tube;

monitoring the polarization resistance and the heat transfer rate of the condenser tube; and controlling the ferrous ion injection and sponge ball cleaning operations, in response to the measured polarization resistance and heat transfer rate, so that the polarization resistance reaches $10^4$ $\Omega cm^2$ while the heat transfer rate does not fall below 95% of the nominal heat transfer rate of the condenser tube, said nominal heat transfer rate being a transfer rate of a new condenser tube.

8. A method according to claim 7, wherein said condenser tube is made of a copper alloy.

* * * * *